(12) United States Patent
Smith et al.

(10) Patent No.: US 9,031,661 B2
(45) Date of Patent: May 12, 2015

(54) MULTI-ELECTRODE CHANNEL CONFIGURATIONS FOR A HEARING PROSTHESIS

(75) Inventors: Zachary M. Smith, Englewood, CO (US); Christopher van den Honert, Englewood, CO (US)

(73) Assignee: Cochlear Limited, Macquarie University, NSW (AU)

(*) Notice: Subject to any disclaimer, the term of this patent is extended or adjusted under 35 U.S.C. 154(b) by 716 days.

(21) Appl. No.: 12/782,604

(22) Filed: May 18, 2010

(65) Prior Publication Data

US 2011/0288613 A1 Nov. 24, 2011

(51) Int. Cl.
- *A61N 1/05* (2006.01)
- *A61N 1/36* (2006.01)
- *H04R 25/00* (2006.01)
- *H03G 9/00* (2006.01)

(52) U.S. Cl.
CPC .......... *A61N 1/36032* (2013.01); *A61N 1/0541* (2013.01); *H03G 9/005* (2013.01); *H04R 25/70* (2013.01)

(58) Field of Classification Search
CPC . A61N 1/0541; A61N 1/323; A61N 1/36032; G01L 2021/065; H03G 9/005
USPC ................ 607/55, 56, 57, 136, 137; 600/547; 381/313, 318
See application file for complete search history.

(56) References Cited

U.S. PATENT DOCUMENTS

| | | | |
|---|---|---|---|
| 4,532,930 A | 8/1985 | Crosby et al. | |
| 4,648,403 A | 3/1987 | Van Compernolle | |
| 5,626,140 A * | 5/1997 | Feldman et al. | 600/484 |
| 5,793,875 A * | 8/1998 | Lehr et al. | 381/313 |
| 6,249,704 B1 | 6/2001 | Maltan et al. | |
| 6,537,200 B2 | 3/2003 | Leysieffer et al. | |
| 6,565,503 B2 | 5/2003 | Leyseiffer | |

(Continued)

FOREIGN PATENT DOCUMENTS

| | | | |
|---|---|---|---|
| WO | 0113991 A1 | 3/2001 | |
| WO | 2004/021885 | 3/2004 | |

(Continued)

OTHER PUBLICATIONS

Boex et al. "Electrical field interactions in different cochlea implant systems" J. Acoust. Soc. Am. vol. 114, Issue 4 pp. 2049-2057 (Oct. 2003).

(Continued)

*Primary Examiner* — Eric D. Bertram
*Assistant Examiner* — Pamela M Bays (57) ABSTRACT

An apparatus and method for determining stimulation channels for a stimulating device is provided. This method and apparatus may involve computing a set of weights for the plurality of stimulation channels of the stimulating hearing prosthesis. These weights may be determined by determining a transimpedance matrix for the stimulating hearing prosthesis where a diagonal of the transimpedance matrix is determined by extrapolation. A transadmittance matrix may then be computed for this transimpedance matrix. An error may then be computed base on positive off-diagonal terms of the transadmittance matrix. The apparatus and method may determine the weights for the stimulation channels by determining an adjustment to the diagonal of the transimpedance matrix that results in a computed error that does not exceed a specified criterion level.

20 Claims, 7 Drawing Sheets

(56) References Cited

U.S. PATENT DOCUMENTS

| | | | |
|---|---|---|---|
| 6,575,894 | B2 | 6/2003 | Leysieffer et al. |
| 6,594,525 | B1 | 7/2003 | Zierhofer |
| 6,594,526 | B2 | 7/2003 | Betzold |
| 6,697,674 | B2 | 2/2004 | Leysieffer |
| 6,754,356 | B1* | 6/2004 | Luo et al. .................. 381/318 |
| 6,778,858 | B1 | 8/2004 | Peeters |
| 7,110,821 | B1 | 9/2006 | Ross |
| 7,184,843 | B1 | 2/2007 | Cohen |
| 7,426,414 | B1 | 9/2008 | Litvak et al. |
| 7,860,573 | B2 | 12/2010 | Honert |
| 2003/0105504 | A1 | 6/2003 | Ziehofer |
| 2005/0187592 | A1 | 8/2005 | Seligman et al. |
| 2005/0192648 | A1 | 9/2005 | Killian et al. |
| 2006/0247735 | A1* | 11/2006 | Honert .................. 607/57 |
| 2007/0135862 | A1 | 6/2007 | Nicolai et al. |
| 2009/0024185 | A1 | 1/2009 | Kulkarni |
| 2010/0198301 | A1 | 8/2010 | Smith |
| 2011/0093038 | A1 | 4/2011 | Honert |

FOREIGN PATENT DOCUMENTS

| | | |
|---|---|---|
| WO | 2006119069 | 11/2006 |
| WO | WO 2010/091177 A1 | 8/2010 |

OTHER PUBLICATIONS

Clopton et al. "Electrode Configuration and Spread of Neural Excitation: Compartmental Models of Spiral Ganglion Cells," Clark & Cowan, International Cochlear Implant, Speech and Hearing Sypmposium, 1995 Ann. Otol. Rhinol. Laryngol, Suppl. 166, pp. 115-118.

Eddington et al. "Auditory Prostheses Reserch WithMultiple Channel Intracochlear Stimulation in Man," Ann Otol Rhinol Laryngol; Nov.-Dec. 1978 87(y Pt 2); 5-39.

European Search Report for 06751841 dated Nov. 9, 2009.

Favre et al. "Channel interactions in patients using the Ineraid multichannel cochlear implant," Hearing Research, Apr. 1993 66(2); 150-6.

International Search Report for PCT/US2006/016353 dated May 17, 2007.

International Search Report for PCT/US2010/023191, dated Mar. 31, 2010.

Jolly et al., "Quadrupolar Stimulation for Cochlear Prostheses: Modeling and Experimental Data," IEEE Trans. Biomd. Eng., vol. 43, No. 8, pp. 857-865, Aug. 1996.

Kral et al., "Spatial Resolution of Cochlear Implants: The Electrical Field and Excitation of Auditory Afferents," Hearing Research 121, pp. 11-28, 1998.

Miyoshi et al., "Proposal of a New Auditory Nerve Stimulation Method for Cochlear Prosthesis," Artifical Organs, 20(8) pp. 941-946, 1996.

Norgia et al., "Measurement of Electrode Current Pulses from Cochlear Implants." Proceedings of the 21st IEEE Como., Italy IEEE May 18-20, 2004, vol. 3, p. 1697-1700.

Rodenhiser et l., "A Solution to the Inverse Problem: A Method for Determining the Driving Curremts for Focused Stimulation," Oct. 31, 1991. New Frontiers of Biomedical Engineering Innovations From Nuclear to Space Technology 13th Annual International Conference of the IEEE Engineering in Medicine and Biology, Society Oct. 31-Nov. 3, 1991, Orlando, Florida, ISA: Proceeding, XPO10102083.

Shannon, Robert V., "Multichannel electrical stimulation of the auditory nerve in man. i. Basic psychophysics." Hearing Research Aug. 1983: 11(2): 157-89.

Suesserman et al. "Lumpedplarameter model for in vivo cochlear stimulation" IEEE Transactions on Biomedical Engineering. vol. 40, Issue: 3. Publication Date: Mar. 1993 pp. 237-245.

Townsend et al. "Reduction of Electrical Interaction in Auditory Prostheses," IEEE Tran. Biomd. Eng., BME-34, No. 11, pp. 891-897, 1987.

Van Compernolle, Dirk, "A Computational Model of the Cochlea used with Cochlear Prosthesis Patients," in Acoustics, Speech, and Signal Processing, IEEE International Conference on ICASSP '85, vol. 10, pp. 427-429, 1985.

Van Compernolle, Dirk, "Speech Processing Strategies for a Multichannel Cochlear Prosthesis," Ph. D., Dissertation, Stanford University, 1985.

van den Honert et al. "Focused intracochlear electric stimulation with phased array channels" Journal of Acoustic Society America 121(6) Jun. 2007, pp. 3703-3716.

Vanpoucke et al. "Identificationof the impedance model of an implanted cochlear prosthesis from intracochler potential measurements," IEEE Transactions on Biomedical Engineering. Publicaton Date: Dec. 2004 vol. 51 Issue: 12, pp. 2174-2183.

White et al. "Multichannel Cochlear Implants" Archives of Otolaryngol. 1984: 110(8); 493-501.

White et al. "Current Spreading and Speech-Processing Strategies for Cochlear prostheses," Clark & Busby International Cochlear Implant Symposium, Ann. Otol. Rhino. Laryng. 96 (Suppl. 128), pp. 22-24, 1987.

Written Opinion for PCT/US2010/023191, dated Mar. 31, 2010.

Rodenhiser et al. "A Method for Determinign the Driving Currents for Focused Stimulationin the Cochlea," IEEE Trans. Biomd. Eng. 4294), pp. 337-342, Apr. 1995.

Townsend et al. "Pitch Perception by Cochlear Implant Subjects," j. Coust. Soc. Am. 82(1); 106-115, 1987.

Office Action for Chinese Application No. 200680023866.8 mailed Sep. 21, 2011 with English Translation (14 pages).

Extended European Search Report for European Application No. 10739119.5 mailed Feb. 26, 2013 (9 pages).

International Search Report for International Application No. PCT/IB2011/052170 mailed Sep. 22, 2011 (5 pages).

International Preliminary Report on Patentability for International Application No. PCT/IB2011/052170 mailed Nov. 29, 2012 (11 pages).

Bonham B H et al., "Current focusing and steering: Modeling, physiology, and psychophysics", Hearing Research, Elsevier Science Publishers, Amsterdam, NL, vol. 242, No. 1-2, Aug. 1, 2008, pp. 141-153.

U.S. Appl. No. 11/414,360, Notice of Allowance mailed on Aug. 20, 2010, 6 Pages.

U.S. Appl. No. 11/414,360, Office Action mailed on Mar. 11, 2010, 11 Pages.

Australian Application No. 2006242390, Office Action mailed Nov. 17, 2010, 3 Pages.

Chinese Application No. 200680023866, Office Action mailed on Jan. 8, 2010, 2 Pages of English Translation.

Japanese Application No. 2008-509192, Office Action mailed on Jan. 25, 2011, 3 Pages of Office Action and 2 Pages of English Translation.

English Translation of Office Action in Chinese Application No. 201180035299.9, mailed Mar. 9, 2015, 18 pages.

* cited by examiner

MULTI-ELECTRODE CHANNEL CONFIGURATIONS FOR A HEARING PROSTHESIS

BACKGROUND

1. Field of the Invention

The present invention relates to a stimulating hearing prosthesis, and more particularly, to using multi-electrode channel configurations in a stimulating hearing prosthesis.

2. Description of the Related Art

To compensate for a deficiency, such as a loss of hearing, several electrical stimulation devices use electrical signals to activate nerve or muscle fibers in a recipient. In particular, a cochlear implant directly stimulates functioning auditory nerves inside the cochlea with electric fields stimulated through electric current pulses. These implant devices typically include a microphone that receives incoming sound and a signal processor that converts selected portions of the incoming sound into corresponding stimulating signals based on a selected sound processing strategy. An internal receiver implanted beneath the skin receives the signals and delivers electric current pulses to an array of electrodes coiled inside the cochlea. The electrodes stimulate the auditory nerve fibers in the cochlea and the resulting electrical sound information is carried along the auditory nerve to the brain for interpretation. Each electrode may provide monopolar or bipolar stimulation. Monopolar stimulation is stimulation delivered from a single intracochlear electrode to a remote extracochlear electrode. Bipolar stimulation occurs when stimulation flows from nearby, paired intracochlear electrodes. Bipolar stimulation focuses the stimulation more and presumably stimulates a smaller, more localized population of auditory nerve fibers. Monopolar stimulation, on the other hand, spreads current over a relatively wider area and stimulates a relatively larger population of neurons.

Using monopolar stimulation, traditional cochlear implants cannot focus stimulation on target neurons that are electrically distant from the stimulating electrodes. For example, in implant devices which use electrodes placed along the length of the scala tympani to stimulate the spiral ganglion cells, there is an inability to focally stimulate small subpopulations of spiral ganglion cells with monopolar stimulation of the placed electrodes. Because the bone surrounding the scalae has an impedance that is relatively higher than the impedance of the perilymph and tissue that fill the scalae, stimulation currents tend to spread longitudinally along the length of the cochlea. Longitudinal current spread results in relatively broad neural excitation patterns compared to those elicited by narrowband acoustic stimulation in healthy ears. Attempts to narrow the broad neural excitation patterns caused by monopolar stimulation have been made using channel configurations with two or more nearby electrodes to source and sink all or some of the current. But, when multiple channels are stimulated simultaneously with the same polarity, electric fields accumulate and neural stimulation patterns combine in a non-linear fashion. While channel configurations of multiple electrodes may result in more focused patterns, there is still usually some significant channel interactions between nearby channels. To avoid the adverse effects of channel interactions, which tend to be greatest with monopolar channel configurations, most traditional implant devices use stimulation strategies that incorporate sequential or temporally "interleaved" stimulation patterns.

SUMMARY

In one aspect of the invention there is provided a method for determining weights for a stimulation channel of a stimulating hearing prosthesis having a plurality of electrodes, wherein the stimulation channel uses the determined weights in providing stimulation using a plurality of the electrodes of the stimulating medical device, the method comprising: determining a transimpedance matrix for the plurality of electrodes; computing a transadmittance matrix for the plurality of electrodes, the transadmittance matrix being a matrix inversion of the transimpedance matrix; computing an error based on positive off-diagonal values of the transadmittance matrix; determining if the error exceeds a criterion level; adjusting a diagonal of the transimpedance matrix if the criterion level is exceeded; calculating the corresponding weights for the plurality of electrodes for the stimulation channel using the adjusted transimpedance matrix; and providing the calculated weights to the stimulating medical device for use in providing stimulation to a recipient of the stimulating medical device.

In another aspect there is provided an apparatus for determining weights for a stimulation channel of a stimulating hearing prosthesis having a plurality of electrodes, wherein the stimulation channel uses the determined weights in providing stimulation using a plurality of the electrodes of the stimulating hearing prosthesis, the apparatus comprising: error minimization module configured to compute a transadmittance matrix by inverting a determined transimpedance matrix, compute an error based on positive off-diagonal values of the transadmittance matrix, determine if the error exceeds a criterion level; and adjust a diagonal of the transimpedance matrix if the criterion level is exceeded; and a weight calculation module configured to calculate corresponding weights for the plurality of electrodes for the stimulation channel; and an interface configured to provide the calculated weights to the stimulating hearing prosthesis for use in providing stimulation to a recipient of the stimulating hearing prosthesis.

BRIEF DESCRIPTION OF THE DRAWING

Embodiments of the present invention are described below with reference to the attached drawings, in which.

DETAILED DESCRIPTION

Aspects of the present invention are generally directed to determining stimulation channels for a stimulating device. In an embodiment, a set of weights for a plurality of stimulation channels of the stimulating hearing prosthesis is determined. First a transimpedance matrix is determined by measuring performing measurement to determine the off-diagonal terms of the transimpedance matrix. As will be discussed in more detail below, this may be accomplished, for example, by stimulating each electrode with a known current and recording the resulting voltages on the un-stimulated electrodes. Then, the diagonal terms of the transimpedance matrix are determined by extrapolation. An iterative process is then employed that inverts the transimpedance matrix to obtain a transadmittance matrix. An adjustment to the diagonal of the transimpedance matrix is then determined based on any positive off-diagonal terms of the transadmittance matrix. Once an adjustment is determined that results in the positive off-diagonal values of the transadmittance matrix having a computed error below a specified criterion level, the determined adjustment is used to determine the set of weights for the stimulations channels. This set of weights is then provided to the stimulating hearing prosthesis for use in applying stimulation to a recipient of the stimulating hearing prosthesis.

Embodiments of the present invention are described herein primarily in connection with one type of stimulating hearing prosthesis, namely a cochlear prostheses (commonly referred to as cochlear prosthetic devices, cochlear implants, cochlear devices, and the like; simply "cochlear implants" herein.) Cochlear implants generally refer to hearing prostheses that deliver electrical stimulation to the cochlea of a recipient. As used herein, cochlear implants also include hearing prostheses that deliver electrical stimulation in combination with other types of stimulation, such as acoustic or mechanical stimulation. It would be appreciated that embodiments of the present invention may be implemented in any cochlear implant or other hearing prosthesis now known or later developed, including auditory brain stimulators, or implantable hearing prostheses that acoustically or mechanically stimulate components of the recipient's middle or inner ear.

Figure 1:
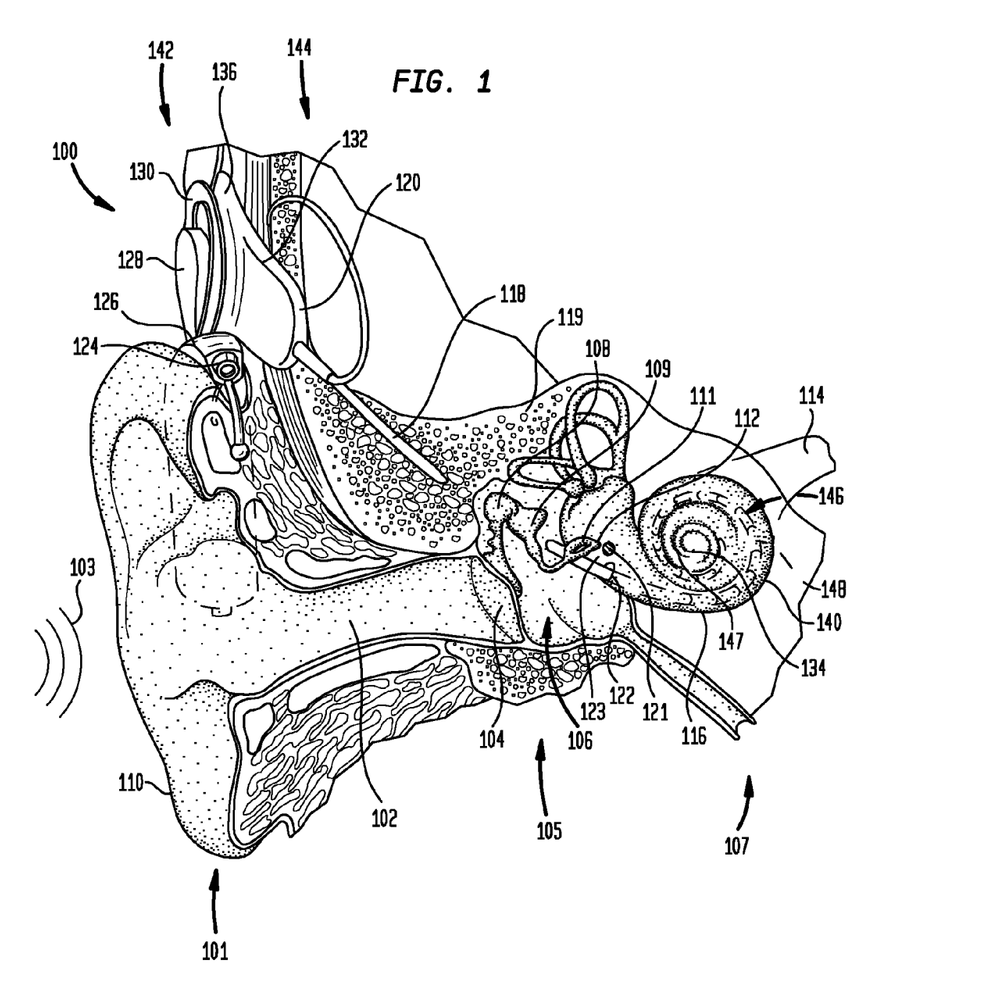
FIG. 1 is perspective view of an exemplary stimulating hearing prosthesis, namely a cochlear implant, in which embodiments of the invention may be implemented.

FIG. 1 is a perspective view of a conventional cochlear implant, referred to as cochlear implant 100 implanted in a recipient having an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant 100 comprises an external component 142 which is directly or indirectly attached to the body of the recipient, and an internal component 144 which is temporarily or permanently implanted in the recipient. External component 142 typically comprises one or more sound input elements, such as microphone 124 for detecting sound, a sound processing unit 126, a power source (not shown), and an external transmitter unit 128. External transmitter unit 128 comprises an external coil 130 and, preferably, a magnet (not shown) secured directly or indirectly to external coil 130. Sound processing unit 126 processes the output of microphone 124 that is positioned, in the depicted embodiment, by auricle 110 of the recipient. Sound processing unit 126 generates encoded signals, sometimes referred to herein as encoded data signals, which are provided to external transmitter unit 128 via a cable (not shown).

Internal component 144 comprises an internal receiver unit 132, a stimulator unit 120, and an elongate stimulating assembly 118. Internal receiver unit 132 comprises an internal coil 136, and preferably, a magnet (also not shown) fixed relative to the internal coil. Internal receiver unit 132 and stimulator unit 120 are hermetically sealed within a biocompatible housing, sometimes collectively referred to as a stimulator/receiver unit. The internal coil receives power and stimulation data from external coil 130, as noted above. Elongate stimulating assembly 118 has a proximal end connected to stimulator unit 120, and a distal end implanted in cochlea 140. Electrode assembly 118 extends from stimulator unit 120 to cochlea 140 through mastoid bone 119, and is implanted into cochlea 104. In some embodiments stimulating assembly 118 may be implanted at least in basal region 116, and sometimes further. For example, stimulating assembly 118 may extend towards apical end of cochlea 140, referred to as cochlear apex 134. In certain circumstances, stimulating assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrode contacts 148, sometimes referred to as array 146 of electrode contacts herein, disposed along a length thereof. Although electrode array 146 may be disposed on stimulating assembly 118, in most practical applications, electrode array 146 is integrated into stimulating assembly 118. As such, array 146 is referred to herein as being disposed in stimulating assembly 118. Stimulator unit 120 generates stimulation signals which are applied by electrode contacts 148 to cochlea 140, thereby stimulating auditory nerve 114.

In cochlear implant 100, external coil 130 transmits electrical signals (i.e., power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding (not shown). In use, implantable receiver unit 132 may be positioned in a recess of the temporal bone adjacent auricle 110 of the recipient.

Because the cochlea is tonotopically mapped, that is, partitioned into regions each responsive to stimulus signals in a particular frequency range, frequencies may be allocated to one or more electrodes of the stimulating assembly to generate an electric field in positions in the cochlea that are close to the region that would naturally be stimulated in normal hearing. This enables the prosthetic cochlear implant to bypass the hair cells in the cochlea to directly deliver electrical stimulation to auditory nerve fibers, thereby allowing the brain to perceive hearing sensations resembling natural hearing sensations. In achieving this, processing channels of the sound processing unit 126, that is, specific frequency bands with their associated signal processing paths, are mapped to a set of one or more electrodes to stimulate a desired nerve fiber or nerve region of the cochlea. Such sets of one or more electrodes for use in stimulation are referred to herein as "electrode channels" or "stimulation channels."

Figure 2:
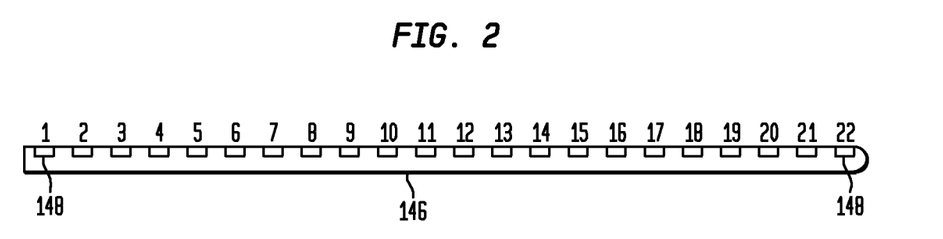
FIG. 2 illustrates a more detailed view of a portion of a stimulating assembly, in accordance with an embodiment.

FIG. 2 illustrates a more detailed view of a portion of a stimulating assembly 118 comprising an array 146 of electrode contacts 148, in accordance with an embodiment. Electrode array 146 may be used to apply different modes of stimulation, such as, for example, monopolar, bipolar, tripolar, or phased-array stimulation. The below discussed embodiments will generally be discussed with reference to a cochlear implant system in which the array 146 provides complex stimulation channels. As used herein, a complex stimulation channel refers to a stimulation channel that uses three or more electrode contacts 148, such as, for example, a phased-array stimulation channel.

In phased-array stimulation, weights are assigned to a plurality of electrodes (e.g., electrodes 1-5, 2-8, all electrodes, etc.) and the stimulation is applied using the weighted electrodes. Phased-array stimulation may also be used in conjunction with a weighted extra-cochlea electrode (not shown). Phased-array stimulation is discussed in more detail in U.S. patent application Ser. No. 11/414,360 by Chris van den Honert, entitled "Focused Stimulation in a Medical Stimulation Device" and Chris van den Honert and David C. Kelsall, "Focused Intracochlear Electric Stimulation with Phase Array Channels," J. Acoust. Soc. Am., 121, 3703-3716 (June 2007), both of which are incorporated by reference herein in the entirety. These references are hereinafter collectively referred to as "the van den Honert references."

Figure 3:
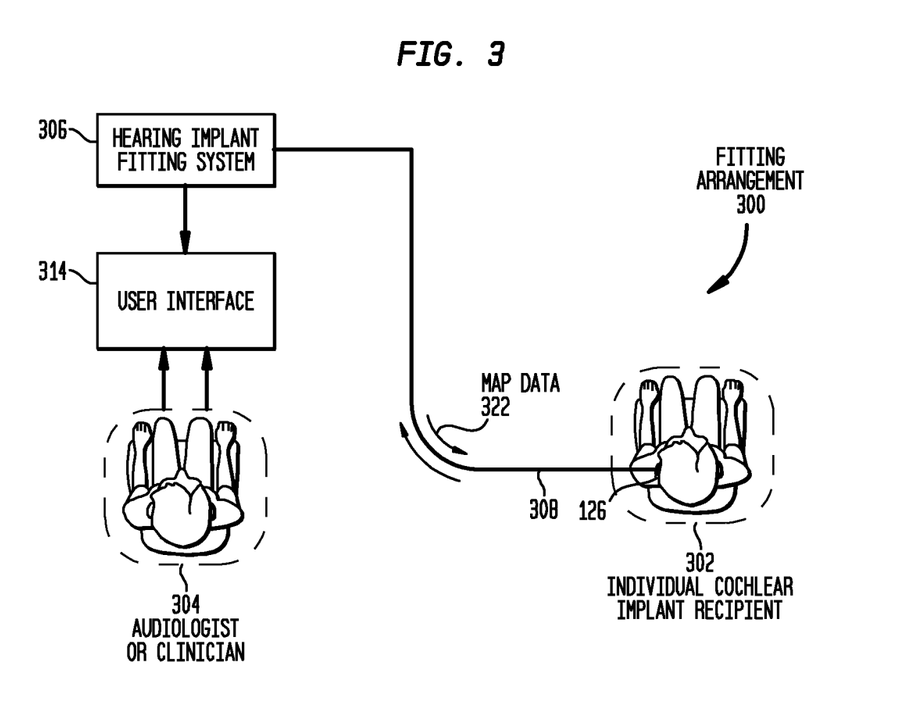
FIG. 3 is a schematic diagram illustrating one exemplary arrangement in which a cochlear implant fitting system may be used to assign and adjust complex stimulation channel electrode weights, in accordance with an embodiment.

FIG. 3 is a schematic diagram illustrating one exemplary arrangement 300 in which a cochlear implant fitting system 306 may be used to assign and adjust complex stimulation channel electrode weights, in accordance with an embodiment. As shown in FIG. 3, an audiologist or clinician 304 may use a cochlear implant fitting system 306 ("fitting system" herein) comprising interactive software and computer hardware to create individualized recipient map data 322 that are digitally stored on system 306 and ultimately downloaded to the memory of the sound processing unit 126 for recipient 302. System 306 may be programmed and/or implement software programmed to carry out one or more of the functions of mapping, neural response measuring, acoustic stimulating, and recording of neural response measurements and other stimuli.

In the embodiment illustrated in FIG. 3, sound processing unit 126 of cochlear implant 100 may be connected directly to fitting system 306 to establish a data communication link 308 between the sound processing unit 126 and fitting system 306. System 306 is thereafter bi-directionally coupled by means of data communication link 308 with sound processing unit 126. It should be appreciated that although sound processing unit 126 and fitting system 306 are connected via a cable in FIG. 3, any communications link now or later developed may be utilized to communicably couple the implant and fitting system.

As an initial matter, audiologist 304 may set up the cochlear implant system 100 and provide the cochlear implant system 100 with an initial set of parameters. This may involve calibrating the cochlear implant 100, as well as determining and setting the threshold and maximum comfortable levels for each stimulation channel of the array 146. An exemplary mechanism for fitting a cochlear implant is provided in U.S. patent application Ser. No. 11/348,309 by James F. Patrick, et al. and entitled "Prosthetic Hearing Implant Fitting Technique," filed Feb. 6, 2006, which is incorporated by reference herein in its entirety. It should be noted however, that this is but one exemplary technique for initially setting up a cochlear implant system, and any technique now or later developed may be used for initially setting up the cochlear implant system. Additionally, during the initial set up, the audiologist may provide a set of default weights to be initially used for each of the stimulation channels.

Figure 4A:
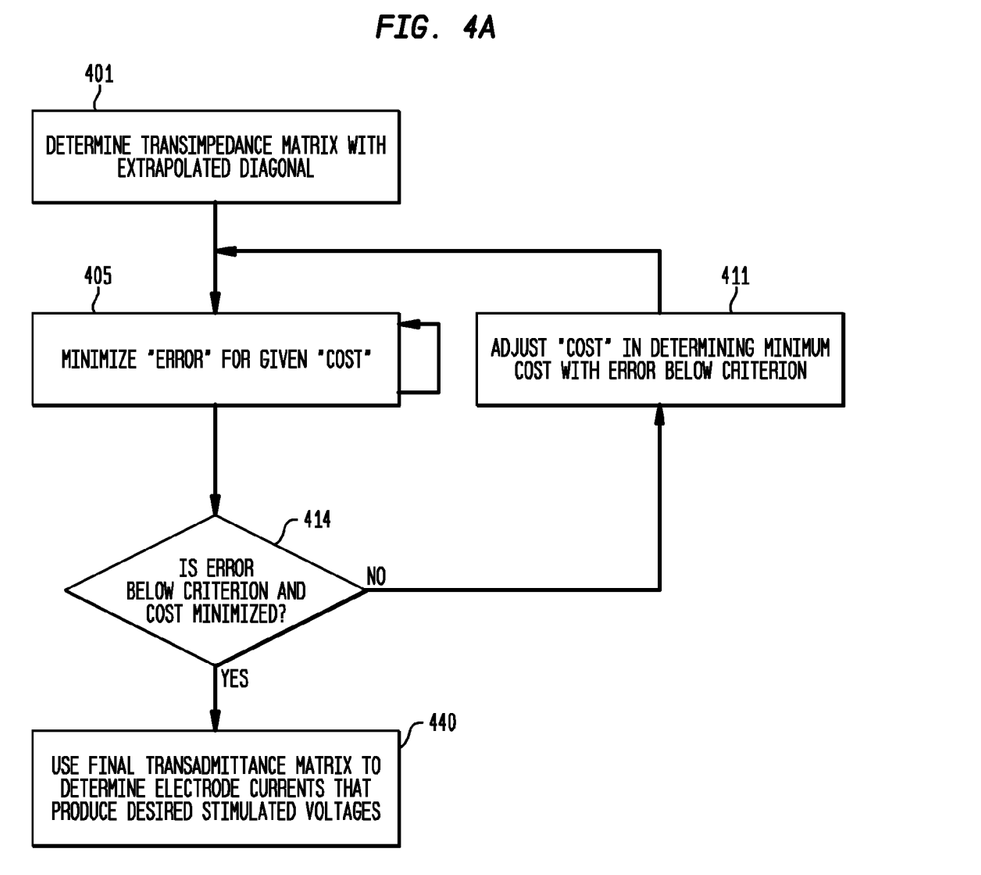
FIG. 4A is a high-level flow chart illustrating operations that may be performed for determining complex stimulation channel weights, in accordance with an embodiment.
Figure 4B:
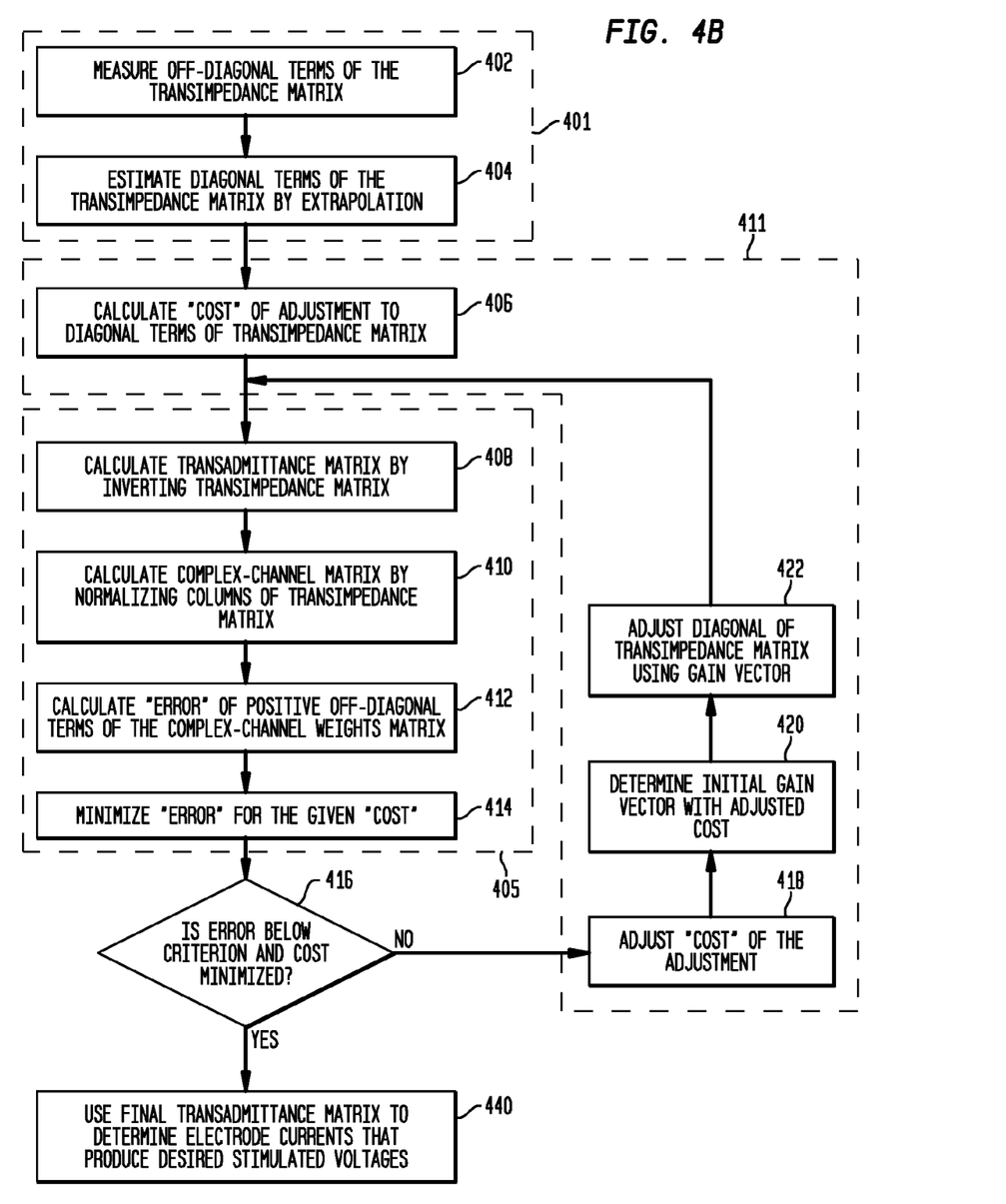
FIG. 4B is a high-level flow chart illustrating operations that may be performed for determining complex stimulation channel weights, in accordance with an embodiment

FIG. 4A is a high-level flow chart illustrating operations that may be performed for adjusting complex stimulation channel weights, in accordance with an embodiment. FIG. 4B provides a more detailed view of the flow chart of the flow chart of FIG. 4A. FIGS. 4A and 4B will be discussed with reference to the fitting system illustrated in FIG. 3. However, it should be noted that this is exemplary only and provided for explanatory purposes, and the general method of FIG. 4A-4B may be used with other types of systems.

For simplicity FIG. 4A will first be described followed by the detailed description of FIG. 4B. As illustrated in FIG. 4A, an audiologist 304 using fitting system 306 may direct fitting system 306 to obtain a transimpedance matrix having a diagonal determined by extrapolation. Then, at block 401, fitting system 306 may perform a minimization routine 405 to determine a gain vector that has a minimum error for a given cost. During the first pass through the routine the cost may be initially set to 0. Fitting system 306 may then, at decision 414, determine if the minimum determined error falls below a specified criterion level and the cost has been minimized. If not, fitting system 306 may, at block 411, adjust the permissible cost (e.g., increase the cost) of the gain vector and pass control back to the error minimization routine 405 to determine the minimum error for this adjusted cost. This process may then repeat until fitting system 306 determines, at decision 414, that the minimum cost has been found with an error below the criterion level. Once found, fitting system 306, at block 440, uses a transadmittance matrix determined using the gain vector having the minimal cost and error below the criterion level to calculate the weights for the phased array stimulation channels of the stimulating hearing prosthesis and provides these weights to the hearing prosthesis for use in providing stimulation to a recipient of the stimulating hearing prosthesis. Each of these block of FIG. 4A will be discussed in more detail below with reference to FIG. 4B.

Figure 5:
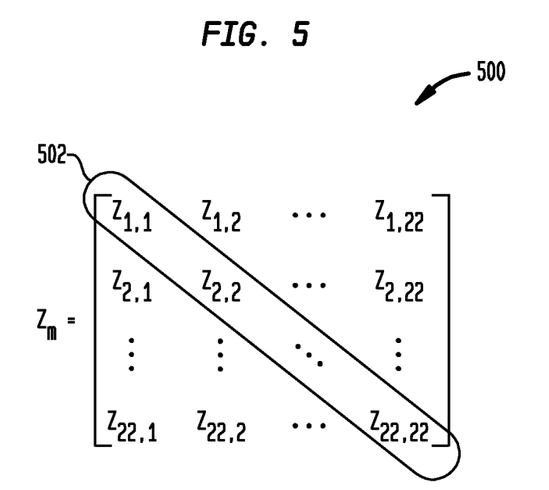
FIG. 5 illustrates an exemplary transimpedance matrix, in accordance with an embodiment of the invention.

As illustrated in FIG. 4B, at block 402, the system 306 obtains the off-diagonal terms of an initial transimpedance matrix. This transimpedance matrix may be obtained, such as, for example, as discussed in the van den Honert references. FIG. 5 illustrates an exemplary transimpedance matrix, $Z_m$, in accordance with embodiments. As illustrated, transimpedance matrix, $Z_m$, 500 comprises 22 columns and 22 rows. Each column and row corresponds to a particular electrode of an exemplary array comprising 22 electrodes, where a row corresponds to the electrode on which stimulation is applied in measuring the transimpedance matrix. And, a column corresponds to the electrode on which the applied stimulation is measured in obtaining the transimpedance matrix.

As discussed in the van den Honert references, all values, except the diagonal, of the transimpedance matrix may be empirically measured by the system 306 stimulating each electrode with a known current, one at a time. Then, the system 306 measures the resulting voltage at each non-stimulated electrode. Because voltage observed on the stimulating electrode includes parts from the bulk resistance and tissue impedance, the diagonal of the transimpendence matrix is not determined in this manner. Rather, at block 404, the values along the diagonal 502 of transimpendence matrix 500 may be estimated by linear extrapolation of the values surrounding the diagonal values. Methods and systems for obtaining the transimpedance matrix and estimating the diagonal values 502 are provided in the above-incorporated by reference van den Honert references, and are not discussed further herein. Although transimpedance matrix, $Z_m$, 500 comprises 22 columns and 22 rows, it should be noted that this is exemplary only, and in other embodiments electrodes arrays comprising a different number of electrodes other than 22 may be used.

At block 406, fitting system 306 calculates the "cost" of any adjustment to the diagonal terms in the transimpedance matrix. Fitting system 306 may calculate this cost by computing the mean of (I-llgain), where gain is a vector of length N, and N is equal to the total number of electrodes (e.g., 22 in this example). As will be discussed in more detail below, the gain vector is a vector used to modify the extrapolated diagonal terms of the transimpedance matrix by multiplying the corresponding values of the gain and the extrapolated diagonal term to provide a new diagonal term for the transimpedance matrix.

In an embodiment, the values of the terms of the gain vector may vary between one and infinity. As such, using the above-noted metric for cost (mean(1−1/gain)), if all values of the gain vector are equal to one, the "cost" will be equal to zero; and, when all values of the gain value are infinity, the "cost" will be one. Thus, in this example, the cost may vary between 0 and 1. Further, in an embodiment, as the gain values increase, the stimulation channel becomes less focused. Thus, a higher "cost" value provides an indication that the channel(s) are less focused than those resulting when the "cost" is lower. As used herein the term focus refers to the concentration of the electric field produced by the stimulation channel during stimulation of the implanted array. For example, if the focus of the stimulation channel is increased, then the resulting electric field is narrowed. Decreasing the focus of the stimulation channel refers to widening the resulting electric field.

Initially, the gain vector may be set so that all values of the gain vector are equal to one. Then, as the process evolves, one or more values of the gain vector may be increased. A further description of exemplary mechanisms for adjusting the gain vector as the process evolves will be presented below.

It should be noted that the above-noted metric for computing the "cost" is but one example of a metric that may be used for computing the "cost." For example, in another embodiment, the "cost" need not be constrained to a value between 0 and 1, but may be computed using another metric such as, for example, computing the mean gain value, where a higher mean gain value would provide an indication that the stimulation channels are less focused than the stimulation channels resulting when the mean gain value is lower.

Fitting system 306, at block 408, inverts the transimpendence matrix to obtain a transadmittance matrix. As will be discussed further below, the transadmittance matrix will be used to determine the set of weights for the phased-array channels. Particularly each column of the inverted transimpedance matrix (also known as the transadmittance matrix) comprises a set of numerical weights (transadmittance values) defining the current contribution from each electrode for producing a non-zero intrascalar voltage at a single discrete stimulation region. As such, each such vector of weights defines a phased-array stimulation channel.

The fitting system 306, at block 410, then calculates a complex-channel matrix by normalizing the columns of the transadmittance matrix. This may be accomplished, for example, by the fitting system 306 determining the maximum value for each column and then dividing each value in the column by the maximum value. Thus, after normalization, the maximum value in any column of the complex-channel matrix would be one (1).

At block 412, fitting system 306 calculates an "error" by summing all positive off-diagonal terms in the complex-channel matrix and then dividing the sum by the number of off-diagonal terms of the matrix. In other words, in an embodiment, fitting system 306 sums all positive terms of the complex-channel matrix other than the terms along the diagonal of the matrix; and, then, divides this sum by the total number of terms of the matrix other than those along the diagonal. The resulting value is referred to as the "error" in this example, because at present, based on modeling of the cochlear, it appears that all off-diagonal terms of a properly determined transadmittance matrix will only have non-positive values. Thus, based on this modeling, it appears that any positive off-diagonal term is an error. In other embodiments, the "error" calculated at block 410 may be computed using a different metric. For example, in an embodiment, the computed "error" may be the mean value of all positive off-diagonal terms, the sum of all positive off-diagonal terms, etc.

Fitting system 306 may then identify the minimum "error" at block 414 for the cost determined at block 408. Various mechanisms may be used for minimizing the error for a given cost at block 414. In one embodiment, block 414 may involve a brute force loop that computes the "error" for every possible gain vector for the cost computed at block 406. This brute force loop may involve, for example, multiplying every possible gain vector with the calculated cost against the diagonal of the transimpedance matrix to adjust the values of the diagonal terms. Then, the transadmittance matrix and complex-channel matrix are computed, such as discussed above, and the "error" calculated for this complex-channel matrix. In other words, a new transimpedance matrix may be calculated for each possible gain vector having a given cost and then repeating blocks 408, 410, and 412 to calculate the error for this transimpedance matrix. Then, after all possible gain vectors having the given cost are checked, fitting system 306 identifies the gain vector with the minimum computed error at block 414.

At decision 416, fitting system 306 checks if this computed error is below a criterion level and whether the "cost" is minimized. In an embodiment, this criterion level may be a threshold value and selected to be, for example, 0.0001; however, in other embodiments, this criterion level may be selected to be a different value, such as, 0.001. The specific number selected for the criterion level may be selected by the designer based on, for example, trials using the disclosed method.

As noted above, in the presently described embodiment, the cost is initially set to zero and then, as will be discussed further below, increased if the error is not below the criterion level. As such, fitting system 306 need not do a separate check in this example to determine if the cost is minimized at block 416 as the cost will always be minimized during each pass through decision 416. However, in other embodiments, fitting system 306 may implement more complex mechanisms in checking if the cost is minimized, such as, for example, in embodiments where the cost is initially high (e.g., closer to one) and then decreased. Or, for example, fitting system 306 may check whether the cost is minimized in embodiments where the cost is adjusted by a particular step size during each pass through the process until a gain vector with the specified cost is found with an error below the criterion level. Then, the step size is decreased and the cost adjusted in order to hone in the minimum cost with a gain vector having an error below the criterion level. A further description of exemplary methods for adjusting the cost will be provided below.

If at decision 416 fitting system 306 determines that the "error" is below the criterion level and the calculated "cost" is minimized, the process proceeds to block 418. If not, the process proceeds to block 440. Each of these paths will be discussed in further detail below.

The above discussed method utilizing a brute force loop for finding the minimum error for a given cost is but one example for finding a gain vector with a minimal cost and an error below the criterion level and in other embodiments other methods may be used. For example, in an embodiment, rather than checking every possible gain vector with a given cost to determine the gain vector with the minimum error, fitting system 306 may simply check possible gain vectors with a given cost until a gain vector is identified that has an error below the criterion level. Then, if an error is found below the criterion level, fitting system 306 deems decision 416 to be satisfied and the process proceeds to block 440.

Or in yet another embodiment, rather than employing a brute force loop to identify the gain vector for a given cost with the minimum "error," fitting system 306 may implement other types of minimization algorithms. For example, in an embodiment, fitting system 306 may use the Sequential Quadratic Programming method, which is a form of medium-scale constrained nonlinear optimization. Each run of such a minimization algorithm may minimize the error as constrained by the given cost. Further, in embodiments using such a minimization algorithm, the above-discussed blocks of 408-410 may be subsumed in block 414 as part of the execution of the minimization algorithm.

If at decision 416, fitting system 306 determines that the "error" does not fall below the criterion level, fitting system 306 then, at block 418, adjusts the cost for the gain vector. For example, during the initial pass through the process, the cost may be set to zero (i.e., the values of all values in the gain vector are equal to one). Then, at block 418 the cost may be increased by a step size (e.g., 0.1, 0.05, 0.01, 0.001, etc). An initial gain vector having the increased cost may be determined at block 420. At block 422, fitting system 306 multiplies each diagonal of the transimpedance matrix (determined at block 404) with the corresponding value from the gain vector. The process then returns to block 408 and fitting system 306 identifies the gain vector with the minimum error as discussed above with reference to blocks 408-416.

This process of increasing the cost by the specified step-size and determining the error for the gain vector with the minimum error is then repeated until fitting system 306 identifies a gain vector with an error less than the criterion level. Once fitting system 306 determines at decision 414, that the criterion are met, the fitting system 306, at block 440, multiples the extrapolated values for the diagonal of the transim-pedance matrix by the gain vector to produce a new diagonal 502 for the transimpedance matrix.

The fitting system 306 may use the final values to generate the electrode weights for stimulation channels and then provide these weights to the cochlear implant 100. For example, fitting system 306 may invert the transimpedance matrix determined at block 418 to determine a transadmittance matrix and then use the values of this transadmittance matrix for the stimulation channel weights. Particularly each column of the transadmittance matrix comprises a set of numerical weights (transadmittance values) defining the current contribution from each electrode for producing a non-zero intrascalar voltage at a single discrete stimulation region. That is, each such vector of weights defines a phased-array stimulation channel. The cochlear implant 100 may then store and use these weights in the sound processing unit 126 and/or the stimulator unit 120.

In another embodiment, fitting system 306 instead of progressing directly to block 440 once an error below the criterion level is met at decision 416 may instead progress to a block (not shown) in which the cost is returned to the cost value for the previous pass through the method in which an error below the criterion level was not found. Then, the step size may be reduced (e.g., by half) and control passed to block 418 to compute a new cost using this reduced step size. Then, fitting system 306 may repeat the process until a gain vector (with the new cost) is found with an error below the criterion level. Then, the step size may be further reduced (e.g., by half) and so on. Using such a mechanism may permit a larger step size to be used initially and then reduced once the process has become more focused on the minimum cost. This may enable the process to more quickly identify the minimum cost with an error below the criterion level.

The above discussed method of FIG. 4 may be viewed as using a dual loop minimization routine where the outer loop identifies the minimum cost and the inner loop identifies the minimum error for a given cost. As discussed above with reference to block 414 various minimization algorithms, such as a Sequential Quadratic Programming method, may be used as the inner loop, where the inner loop identifies the minimum error as constrained by cost. In other embodiments, both the inner loop and outer loop may use various types of minimization algorithms. For example, although the above discussed process was discussed with reference to the outer loop being a brute force type loop where the cost is increased until the criterion level for the error is met, in other embodiments, the outer loop may use other types of minimization algorithms such as the Sequential Quadratic Programming method. In other words, a wide variety of minimization algorithms could be used in different embodiments without departing from the invention.

As noted above, the above discussed embodiments may be used to determine electrode weights for customized complex-channel configurations for an individual ear. This may enable the cochlear implant 100 to provide narrow neural excitation patterns and an increased number of independent channels. These embodiments may also raise the upper limit on stimulation rates over conventional systems because multiple channels can be stimulated simultaneously, and also provide for better spectral resolution and reduced channel interactions.

Figure 6:
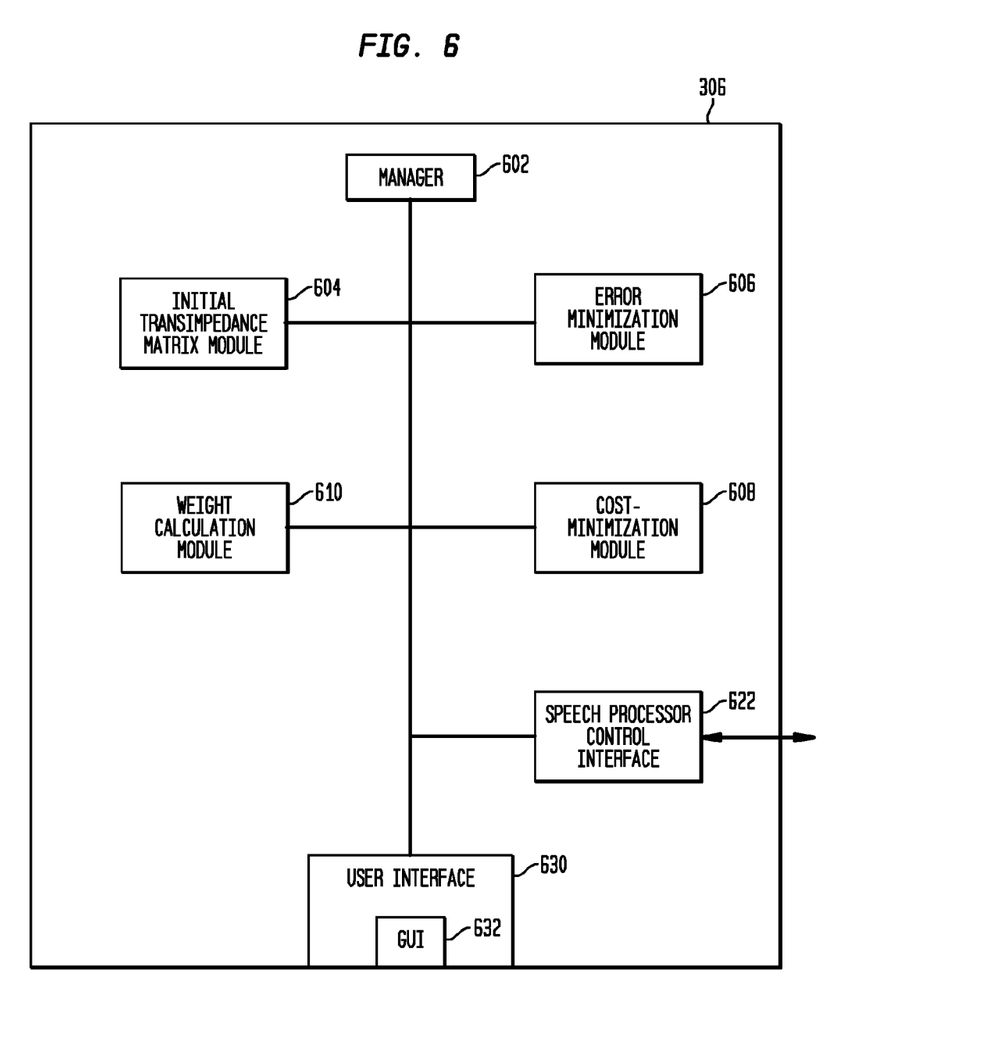
FIG. 6 is a high-level functional block diagram of cochlear implant fitting system in accordance with an embodiment.

FIG. 6 is a high-level functional block diagram of cochlear implant fitting system 306 in accordance with an embodiment of the present invention. The primary components and operative aspects of fitting system 306 are shown in block diagram form for ease of description and it should be understood that these blocks may be split apart or combined in numerous other ways. In the exemplary embodiment shown in FIG. 6, the components are shown as being coupled by a communications bus. However, it is to be understood that the components of fitting system 306 may be connected in any manner suitable for the particular application.

As illustrated, fitting system 306 comprises a manager 602, initial transimpedance matrix module, 604, error minimization module 606, cost minimization module 608, weight calculation module 610, speech processor control interface 622, and user interface 630. Manager 602 performs general operations and controls the other components shown in FIG. 6. Speech processor control interface 622 may provide an interface for connecting fitting system 306 to the speech processor of cochlear implant 100 via data communication link 308.

Initial transimpedance matrix measurement module 604 may be responsible for determining the initial transimpedance matrix and extrapolating the values for the diagonal of this initial transimpedance matrix such as, for example, the above-discussed blocks 402 and 404 of FIG. 4.

Error minimization module 606 may be responsible for determining the gain vector with the minimum error for a given cost, such as was discussed above with reference to blocks 408-416 of FIG. 4. Cost minimization module 608 may be responsible for determining the minimum cost with a gain vector having an error satisfying the criterion level, such as was discussed above with reference to blocks 406 and 418-422 of FIG. 4. In an embodiment implementing a dual loop minimization procedure, such as discussed above, error minimization module 606 may be responsible for execution of an inner loop minimization routine and cost minimization module may be responsible for executing an outer loop minimization routine.

User interface 630 may include any interface which is used by audiologist/clinician 304 to communicate with fitting implant system 306 via user interface 314. The audiologist/clinician 304 can provide input using any one or combination of known methods, including a computer keyboard, mouse, voice-responsive software, touch-screen, retinal control, joystick, and any other data entry or data presentation formats now or later developed.

In the embodiment illustrated in FIG. 6, user interface 630 may include a graphical user interface (GUI) 608 which is displayed by user interface 314, above. The audiologist/clinician 304 may use user interface to interact with use a graphical user interface (GUI) 632 in determining the off-diagonal terms of the initial transimpedance matrix in conjunction with initial transimpedance matrix measurement module 604. Additionally, the GUI 632 may be used while setting up the cochlear implant, such as, for example, to input/receive information when determining the initial threshold and maximum comfort levels for each electrode of the array.

As illustrated in FIG. 6, fitting system 306 may also comprise a weight calculation module 610 that determine the weights for each stimulation channel. For example, in a cochlear implant system employing phased-array stimulation channels, weight calculation module 610 may be responsible for inverting the transimpedance matrix and determining the weights for each channel such as discussed above with reference to block 440 of FIG. 4. Further weight calculation module 610 may also transform the determined weights and other data (e.g., threshold and maximum comfort level data) to implant-based map data 322 for the cochlear implant 100. This map data 322 may be in any form suitable for the implemented cochlear implant 100. This map data 322 generated by data transformer 616 may then be provided to the sound processing unit 126 via speech processor control interface 622.

The subject matter described herein may be embodied in various systems, apparatus, methods, and/or articles depending on the desired configuration. Particularly, various implementations of the subject matter described, such as the embodiment of FIG. 6, components may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, applications, components, or code) include machine instructions for a programmable processor, and may be implemented in a high-level procedural and/or object-oriented programming language, and/or in assembly/machine language. As used herein, the term "machine-readable medium" refers to any computer program product, computer-readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. Similarly, systems are also described herein that may include a processor and a memory coupled to the processor. The memory may include one or more programs that cause the processor to perform one or more of the operations described herein.

All documents, patents, journal articles and other materials cited in the present application are hereby incorporated by reference.

Embodiments of the present invention have been described with reference to several aspects of the present invention. It would be appreciated that embodiments described in the context of one aspect may be used in other aspects without departing from the scope of the present invention.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart there from.

The foregoing description has been directed to specific embodiments of this invention. It will be apparent; however, that other variations and modifications may be made to the described embodiments, with the attainment of some or all of their advantages. Therefore, it is the object of the appended claims to cover all such variations and modifications as come within the true spirit and scope of the invention

What is claimed is:

1. A method for determining weights for a stimulation channel of a stimulating hearing prosthesis having a plurality of electrodes, wherein the stimulation channel uses the determined weights in providing stimulation using a plurality of the electrodes of the stimulating medical device, the method comprising:
   determining a transimpedance matrix for the plurality of electrodes;
   computing, at an error minimization module, a transadmittance matrix for the plurality of electrodes, the transadmittance matrix being a matrix inversion of the transimpedance matrix;
   computing, at the error minimization module, an error value based on positive off-diagonal values of the transadmittance matrix; determining if the error value exceeds a criterion level value;
   adjusting, at the error minimization module, a diagonal of the transimpedance matrix in response to determining that the criterion level value is exceeded;
   calculating, at a weight calculation module, the corresponding weights for the plurality of electrodes for the stimulation channel using the adjusted transimpedance matrix; and
   providing, via an interface, the calculated weights to the stimulating medical device for use in providing stimulation to a recipient of the stimulating medical device.

2. The method of claim 1, wherein the steps of computing a transadmittance matrix, computing an error value, determining if the error value exceeds a criterion level value, and adjusting the diagonal are repeated until the step of determining if the error value exceeds the criterion level value determines that the error value does not exceed the criterion level value.

3. The method of claim 1, further comprising:
computing, at the error minimization module, a complex channel matrix by normalizing at least one column of the computed transadmittance matrix; and
wherein computing an error value comprises computing the error value based on positive off-diagonal values of the complex channel matrix.

4. The method of claim 1, wherein the stimulating medical device is a cochlear implant.

5. The method of claim 1, further comprising:
executing, at the error minimization module, a minimization algorithm to determine a set of one or more gain values for adjusting the diagonal of the transimpedance matrix that results in a determined error value that does not exceed the criterion level value.

6. The method of claim 5, wherein the minimization algorithm uses a sequential quadratic programming method to obtain the set of one or more gain values by determining the set of one or more gain values that provides the minimum error value for the determined cost.

7. The method of claim 5, further comprising:
determining, at a cost minimization module, a cost based on the set of one or more gain values; and
wherein the minimization algorithm identifies a set of one or more gain values, with the determined cost, that provides an error value that does not exceed the criterion level value.

8. The method of claim 7, wherein determining a cost comprises:
adjusting, at the cost minimization module, the determined cost to determine a minimal cost in which the minimization algorithm identifies a set of one or more gain values, with the determined cost, that provides an error value that does not exceed the criterion level value.

9. The method of claim 7, wherein the minimization algorithm terminates upon identifying a set of one or more gain values, for the determined cost, that provides an error value that does not exceed the criterion level value.

10. An apparatus for determining weights for a stimulation channel of a stimulating hearing prosthesis having a plurality of electrodes, wherein the stimulation channel uses the determined weights in providing stimulation using a plurality of the electrodes of the stimulating hearing prosthesis, the apparatus comprising:
an error minimization module configured to compute a transadmittance matrix by inverting a determined transimpedance matrix, compute an error value based on positive off-diagonal values of the computed transadmittance matrix, determine if the error value exceeds a criterion level value, and adjust a diagonal of the transimpedance matrix in response to determining that the criterion level value is exceeded;
a weight calculation module configured to calculate corresponding weights for the plurality of electrodes for the stimulation channel; and
an interface configured to provide the calculated weights to the stimulating hearing prosthesis for use in providing stimulation to a recipient of the stimulating hearing prosthesis.

11. The apparatus of claim 10, wherein the error minimization module is configured to repeat, until the minimization module determines an error value that does not exceed the criterion level value, the steps of computing a transadmittance matrix, computing an error value, determining if the error value exceeds a criterion level value, and adjusting the diagonal.

12. The apparatus of claim 10, wherein the error minimization module is further configured to compute a complex channel matrix by normalizing at least one column of the computed transadmittance matrix, and wherein, in computing an error value, the error minimization module is configured to compute the error value based on positive off-diagonal values of the complex channel matrix.

13. The apparatus of claim 10, wherein the stimulating hearing prosthesis is a cochlear implant.

14. The apparatus of claim 10, wherein the error minimization module is configured to execute a minimization algorithm to determine a set of one or more gain values for adjusting the diagonal of the transimpedance matrix that results in a determined error value that does not exceed the criterion level value.

15. The apparatus of claim 14 further comprising:
a cost minimization module configured to determine a cost based on the set of one or more gain values; and
wherein the minimization algorithm is configured to identify a set of one or more gain values, with the determined cost, that provides an error value that does not exceed the criterion level value.

16. The apparatus of claim 15, wherein the cost minimization module in determining a cost is configured to adjust the determined cost to determine a minimal cost in which the minimization algorithm identifies a set of one or more gain values, with the determined cost, that provides an error value that does not exceed the criterion level value.

17. The apparatus of claim 15, wherein the minimization algorithm uses a sequential quadratic programming method to obtain the set of one or more gain values by determining the set of one or more gain values that provides the minimum error value for the determined cost.

18. The apparatus of claim 15, wherein the minimization algorithm is configured to terminate upon identifying a set of one or more gain values, for the determined cost, that provides an error value that does not exceed the criterion level value.

19. A computer program embodied on a non-transitory computer readable medium, the computer program comprising program code for controlling a processor to execute a method for determining weights for a stimulation channel of a stimulating hearing prosthesis having a plurality of electrodes, wherein the stimulation channel uses the determined weights in providing stimulation using a plurality of the electrodes of the stimulating hearing prosthesis, the method comprising:
determining a transimpendance matrix for the plurality of electrodes;
computing a transadmittance matrix for the plurality of electrodes, the transadmittance matrix being a matrix inversion of the transimpedance matrix;
computing an error value based on positive off-diagonal values of the transadmittance matrix; determining if the error value exceeds a criterion level value;
adjusting a diagonal of the transimpedance matrix in response to determining that the criterion level value is exceeded; calculating the corresponding weights for the plurality of electrodes for the stimulation channel using the adjusted transimpedance matrix; and
providing the calculated weights to the stimulating hearing prosthesis for use in providing stimulation to a recipient of the stimulating hearing prosthesis.

20. An apparatus for determining weights for a stimulation channel of a stimulating device having a plurality of electrodes, wherein the stimulation channel uses the determined weights in providing stimulation using a plurality of the electrodes of the stimulating hearing prosthesis, the apparatus comprising:
- means for determining a transimpendance matrix for the plurality of electrodes;
- means for computing a transadmittance matrix by inverting the transimpedance matrix; means for computing a transadmittance matrix for the plurality of electrodes, the transadmittance matrix being a matrix inversion of the transimpedance matrix
- means for determining if the error value exceeds a criterion level value;
- means for adjusting a diagonal of the transimpedance matrix in response to determining that the criterion level value is exceeded;
- means for calculating the corresponding weights for the plurality of electrodes for the stimulation channel using the adjusted transimpedance matrix; and
- means for providing the calculated weights to the stimulating hearing prosthesis for use in providing stimulation to a recipient of the stimulating hearing prosthesis.

* * * * *